US010561421B2

(12) United States Patent
Scholten et al.

(10) Patent No.: US 10,561,421 B2
(45) Date of Patent: Feb. 18, 2020

(54) JAW PIECE WITH A LAYERED CONSTRUCTION, FOR A SURGICAL INSTRUMENT

(71) Applicant: Aesculap AG, Tuttlingen (DE)

(72) Inventors: Thomas Scholten, Tuttlingen (DE); Gunnar Wanke, Kreuzlingen (CH)

(73) Assignee: Aesculap AG (DE)

( * ) Notice: Subject to any disclaimer, the term of this patent is extended or adjusted under 35 U.S.C. 154(b) by 345 days.

(21) Appl. No.: 15/306,291

(22) PCT Filed: Apr. 24, 2015

(86) PCT No.: PCT/EP2015/058942
§ 371 (c)(1),
(2) Date: Oct. 24, 2016

(87) PCT Pub. No.: WO2015/165819
PCT Pub. Date: Nov. 5, 2015

(65) Prior Publication Data
US 2017/0049446 A1 Feb. 23, 2017

(30) Foreign Application Priority Data
Apr. 28, 2014 (DE) .................. 10 2014 207 971

(51) Int. Cl.
*A61B 17/10* (2006.01)
*A61B 17/29* (2006.01)

(52) U.S. Cl.
CPC .............. *A61B 17/10* (2013.01); *A61B 17/29* (2013.01); *A61B 2017/294* (2013.01); *A61B 2017/2926* (2013.01); *A61B 2017/2933* (2013.01)

(58) Field of Classification Search
CPC ... A61B 17/1285; A61B 17/10; A61B 17/105; A61B 17/122; A61B 17/128;
(Continued)

(56) References Cited

U.S. PATENT DOCUMENTS 5,358,506 A 10/1994 Green
5,858,018 A 1/1999 Shipp et al.
(Continued)

FOREIGN PATENT DOCUMENTS

CN 1655726 A 8/2005
CN 102614003 A 8/2012
(Continued)

OTHER PUBLICATIONS

German Search Report for German Application No. 10 2014 207 971.3, dated Mar. 13, 2015 with translation, 15 pages.
(Continued)

*Primary Examiner* — Ryan J. Severson
*Assistant Examiner* — Mohamed G Gabr
(74) *Attorney, Agent, or Firm* — RatnerPrestia

(57) ABSTRACT

A jaw member for a tubular shafted surgical instrument includes a first branch having a first active region and a second branch having a second active region. The first branch and/or the second branch has a respective link member, and the branches are held in the axial direction. A cam support member is slideable relative to the at least one link member in the axial direction. The at least one link member and the cam support member are formed substantially planar and are arranged substantially layerlike one above the other. A corresponding jaw member can be assembled onto a tubular shaft.

16 Claims, 6 Drawing Sheets

(58) Field of Classification Search
CPC .............. A61B 17/12; A61B 17/00234; A61B 17/0682; A61B 17/083; A61B 17/29; A61B 17/072; A61B 17/3201; A61B 17/068; A61B 2090/0803; A61B 2090/0811; A61B 2090/0807; A61B 2090/0814; A61B 90/08; A61B 2017/00407; A61B 2017/00115; A61B 2017/00734; A61B 2017/00367; A61B 2017/2926; A61B 2017/12004; A61B 2017/2923; A61B 2017/2927; A61B 2017/00778; A61B 2017/2943; A61B 1/3132; A61B 2017/2902; A61B 2017/2932; A61B 2017/2933; A61B 2017/2937; A61B 2017/294

See application file for complete search history.

(56) References Cited

U.S. PATENT DOCUMENTS

| | | | |
|---|---|---|---|
| 6,155,988 | A | 12/2000 | Peters |
| 6,228,097 | B1 | 5/2001 | Levinson |
| 6,896,684 | B2 | 5/2005 | Monassevitch et al. |
| 2005/0043757 | A1 | 2/2005 | Arad et al. |
| 2005/0171560 | A1 | 8/2005 | Hughett |
| 2006/0085015 | A1* | 4/2006 | Whitfield ............... A61B 17/10 606/142 |
| 2006/0235437 | A1 | 10/2006 | Vitali et al. |
| 2006/0235442 | A1 | 10/2006 | Huitema |
| 2008/0140090 | A1 | 6/2008 | Aranyi et al. |
| 2010/0137886 | A1 | 6/2010 | Zergiebel et al. |
| 2011/0087243 | A1 | 4/2011 | Nguyen et al. |
| 2011/0295270 | A1 | 12/2011 | Giordano et al. |
| 2012/0197269 | A1* | 8/2012 | Zammataro ............ A61B 17/10 606/142 |
| 2012/0310259 | A1 | 12/2012 | Sorrentino et al. |
| 2013/0151870 | A1 | 6/2013 | Morales |
| 2014/0379003 | A1 | 12/2014 | Blake, III et al. |
| 2017/0049446 | A1 | 2/2017 | Scholten et al. |
| 2017/0367688 | A1* | 12/2017 | Scholten ............ A61B 17/1285 |

FOREIGN PATENT DOCUMENTS

| | | | |
|---|---|---|---|
| DE | 2744816 | | 4/1978 |
| DE | 69220110 | | 10/1997 |
| DE | 202010005263 | U1 | 6/2010 |
| DE | 102010036713 | | 2/2012 |
| DE | 202011109957 | U1 | 7/2012 |
| EP | 0945105 | | 9/1999 |
| EP | 1712187 | | 10/2006 |
| EP | 2481360 | | 8/2012 |
| WO | 2006042110 | | 4/2006 |
| WO | 2006042141 | | 4/2006 |
| WO | WO-2006042141 | A2 * | 4/2006 ............. A61B 17/10 |
| WO | 2008118928 | | 10/2008 |
| WO | 2008127968 | A2 | 10/2008 |

OTHER PUBLICATIONS

Chinese Office Action for Chinese Application No. 201580023303.8, dated Aug. 23, 2018, with translation, 17 pages.
Chinese Office Action for Chinese Application No. 201580021985.9, dated Jul. 31, 2018, with translation, 22 pages.
Non Final Office Action for U.S. Appl. No. 15/306,277, dated Jan. 2, 2019—28 pages.
German Search Report for German Application No. 10 2014 207 900.4, dated Mar. 17, 2015 with translation, 15 pages.
International Search Report and Written Opinion of the International Authority for International Application No. PCT/EP2015/058948, 8 pages.
International Search Report and Written Opinion for International Application No. PCT/EP2015/058942, 10 pages.
Notice of Allowance for U.S. Appl. No. 15/306,277, dated Jul. 25, 2019, 15 pages.

* cited by examiner

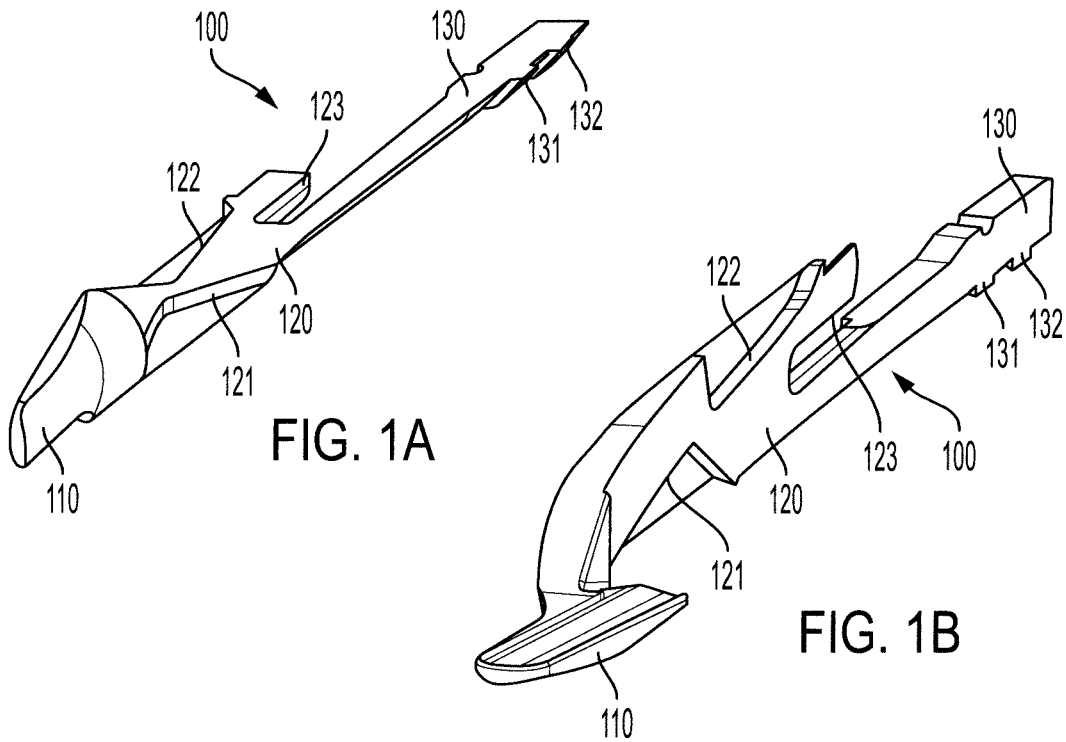
FIG. 1A
FIG. 1B
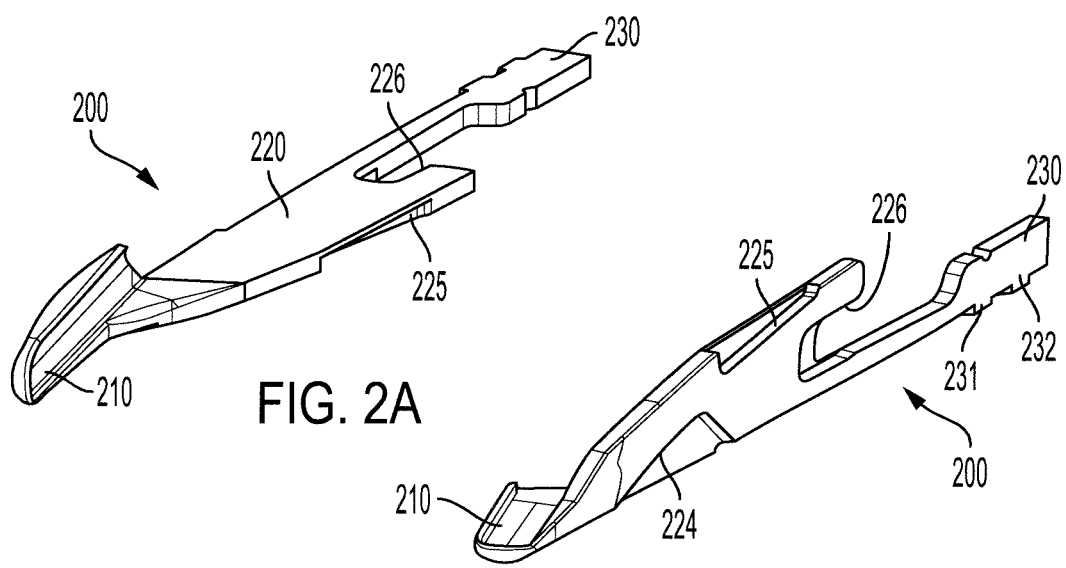
FIG. 2A
FIG. 2B

JAW PIECE WITH A LAYERED CONSTRUCTION, FOR A SURGICAL INSTRUMENT

RELATED APPLICATION(S)

This is the United States national phase entry of International Application No. PCT/EP2015/058942, filed Apr. 24, 2015, which is related to and claims the benefit of priority of German Application No. DE 10 2014 207 971.3, filed Apr. 28, 2014. The contents of International Application No. PCT/EP2015/058942 and German Application No. DE 10 2014 207 971.3 are incorporated by reference herein in their entireties.

FIELD

The present invention relates to a jaw member or jaw assembly for/of a surgical tubular shafted instrument, and in particular a jaw member or jaw assembly in which link members of a link motion are formed at the rear end of branches/arms of the jaw assembly. A surgical tubular shafted instrument, for example, is an endoscopic tubular shafted instrument for applying surgical clips.

BACKGROUND

In the prior art some jaw members for tubular shafted surgical instruments are known. In European Patent Application EP 1 712 187 A2, for example, a jaw member is shown in which the two branches are connected elastic resiliently on a common base. In the region of their distal ends which are intended to hold the surgical clip and to press the surgical clip together and to apply the clip thereby the two branches exhibit on their outer sides a sliding surface, respectively. To close the jaw member and thus to apply the clip, the jaw member is shifted to proximal relative to the shaft in which it is arranged (thus the jaw member is partly drawn towards the handle member into the shaft or the shaft is pushed over the jaw member) and the distal edge of the shaft slides along the sliding surfaces. Through the inclination of the sliding surfaces relative to the axis of the shaft, the distal ends of the branches are urged inward, while the proximal ends of the branches are held by the base.

In this way the branches perform a rotational movement, respectively, around the point at which the branches are connected to the base. An opening operation of the jaw member is done without a guidance and is exclusively guaranteed by the elasticity of the branches that urge in the original position when the jaw member during opening operation is pushed out of the shaft.

A comparable jaw member is also shown in the International Patent Application WO 2008/127 968, even when the instrument shown there overall differs greatly from the instrument described above.

Even more significant is the rotational movement of the branches during opening and closing of the jaw member from the US patent application US 2005/0171560 A1. There the distal regions of both branches are hinged to the base and rotate around the attachment point. Also at this construction the clip is applied by the distal edge of the shaft which is sliding onto the sliding surfaces, which are provided on the outer sides of the branches, and thus pressing the branches inwards.

The problem with this kind of jaw members is that they have always the same closing geometry, more specifically, that at first always the distal ends of the branches touch each other or slide past each other and that the contact or the past sliding of each other of the more proximal regions of branches follows. In clip applicators this means that the clip is always closed from the distal end. For other surgical instruments such as endoscopic scissors for example this design of a jaw member is not useful for this reason.

Another problem with this kind of jaw members is that the opening movement of the jaw member/jaw assembly is realized only by the elasticity of the branches/arms of the jaw member/jaw assembly. The opening movement of the jaw member is done without any guiding. Should a piece of tissue or another part/obstacle end up between the front edge of the shaft and a branch/arm of the jaw member/assembly, could this hinder the opening operation of the jaw member/assembly, then the instrument first has to be removed from the patient's body to remove the tissue/obstacle to be subsequently reintroduced into the patient. This leads to delays and disturbances in the operation flow.

SUMMARY

The object of the present invention is to provide a jaw member/jaw assembly for/of a tubular shafted surgical instrument, which makes it possible to introduce clips from a magazine from the proximal end into the jaw member/jaw assembly, a method for assembling a jaw member/jaw assembly for/of a tubular shafted surgical instrument and a method for assembling a tubular shafted surgical instrument.

The object of the present invention is achieved by a jaw member/jaw assembly and methods as described herein.

Definition of Expressions

The term of the "surgical tubular shafted instrument" in this application comprises at first endoscopic instruments such as endoscopic clip applicators or needle holders. On the other hand this term also comprises surgical instruments for an open surgery, in which the function portion and/or the active portion/mouth part of the instrument are separated/distanced by a shaft or a shaft-like component from the operating portion or handle portion. The term "shaft" or "shaft-like component" here refers to a component whose dimensions and location vis-à-vis the operating portion (for example, handle) is substantially invariable during an operation of the surgical instrument. An axial displacement along the axis of the shaft or shaft-like component or a rotation around this axis is allowed, but not a substantial displacement transverse to this axis or a rotation with respect to this axis in such a way that the two ends of the component substantially move away from this axis. Preferably, the length of a shaft or shaft-like component is larger than its two other dimensions (width, depth) and it is further preferably formed thin. The shaft or the shaft-like component don't have to be round, closed, tubular or thin walled. It is crucial here that it is an instrument which not like an ordinary pair of scissors has a pivot in which all the essential elements of the instrument turn around, but that the power to open and close the jaw member/jaw assembly is transmitted via a relative axial movement of a component in relation to the shaft.

The "function portion" or "active portion" in this application is the region of the surgical tubular shafted instrument in which the actual function is executed. At a needle holder this is the region that engages and holds the needle thus the distal regions of the branches/arms. At a pair of scissors it is the region which severs the tissue or something else, thus the region at which the two shearing edges sliding on each other are formed. At a clip applicator it is the region in which the clip is initially held, while the clip is brought into the correct position and the correct state by the surgeon, and in which the clip is then subsequently applied, i.e. pressed. At other instruments, the definition of the function portion or active portion shall apply accordingly.

The "active region" is the region of a single branch/arm, at which the branch/arm causes the intended function of the instrument thus at a needle holder a gripping portion and at a pair of scissors a shearing edge and a clip applicator a contact region of the clip.

A "closing" or a "closing operation" of the jaw member/assembly here means that the active regions of the branches/arms moving towards each other during the closing operation. In case of a pair of scissors the active regions of the branches/arms move, thus the shearing edges, in the late process of the closing process passing each other and, therefore, move again apart from each other. This whole process is known as closing operation of the jaw member/assembly. Generally speaking a closing operation designates the execution of the function assigned to the instrument such for example the gripping of a tissue or, for example, a needle, a cutting of tissue or other objects, an application of a clip or spreading of tissue or other objects such as, for example, a clip. An adjoining "opening" or an adjoining "opening operation" generally designates then the return of branches/arms, also as well as the active regions or the distal regions of the branches/arms of the jaw member/assembly of the respective instrument, in their initial position(s). At a surgical retractor the assignment is the other way around, thus it performs its task when the branches/arms substantially move away from each other, so performing an opening operation, whereas a return of the branches/arms to the initial position(s) corresponds to a closing operation. Nevertheless, at such an instrument exists a clear opening operation and a clear closing operation.

According to a first aspect of the present invention a jaw member/jaw assembly for/of a surgical tubular shafted instrument comprising a first branch/arm having a first active region and a second branch/arm having a second active region. The first branch/arm and/or the second branch/arm have a respective link member (of a link motion) and the branches/arms are held/orientated in the axial direction. In addition, a cam support member is provided which is slideable in the axial direction relative to at least one link member, wherein said at least one link member and the cam support member are formed substantially planar and are arranged substantially layerlike one above the other.

With the jaw member/Jaw assembly of the present invention it is possible to construct and arrange the links and the cam support member in such a way that the resulting assembly in a region away from the active portion of the jaw member at least in a direction transverse to the longitudinal axis of the jaw member has a considerably smaller dimension than in the region of the active portion of the jaw member. In this way, it is possible to introduce/insert a surgical clip from the rear thus from proximal into the active portion of the jaw member. When such a clip is then applied by pressing and is then removed laterally or distally from the active portion of the jaw member (mostly by pulling the tubular shafted instrument back), a further clip can be introduced into the active portion with a suitable feeding system from a magazine from proximal. Some feeding systems for regular surgical clips are known in the prior art. The jaw member/jaw assembly of the present invention, however makes it possible to introduce/insert double-shank clips from proximal to the active portion of the jaw member. This also applies for tubular shafted instruments with a very small outer diameter of approximately 5 mm. In the prior art, such a jaw member/jaw assembly is not known, because in such dimensions the components must be made very delicate and therefore the transmission of the necessary forces is no longer possible. Only the usage of link members for controlling the opening operation and particularly the closing operation and the layered (sandwich-like) arrangement of these link members makes it possible to supply such double-shank clips in this way. For applications other than clip applicators or clip applicators with larger shank diameter the jaw member/jaw assembly of the present invention has the advantage that significant greater forces can be transmitted to the active portion, as it is the case in the respective same shaft diameter in the prior art.

In order to cause a relative movement between the at least one link member and the cam support member, a (one) component must be held at least axially. This can be done either by a separate retaining member, or a member of the tubular shaft of a tubular shafted instrument performs this function, for example the shaft wall. The retaining member can also denote a member of the tubular shaft that is adapted to ensure the axial bearing of the respective cam member. This also applies to all other embodiments of the jaw member described herein.

According to an advantageous embodiment of the first aspect of the present invention, the cam support member and at least one link member exhibit at least one region in which they form an undercut. In this way, a lifting of the link member from the cam support member is prevented. It is therefore no longer necessary to provide a component which prevents a lifting of the components from one another, which would lead to a blockage of the space through which a clip or double-shank clip is inserted from proximal into the active portion of the jaw member. On the one hand this reduces the number of required components and increases the other hand, the free space available. Preferably at least a region of an undercut is present over the entire range of movement of the link member to the cam support member from a fully open position to a fully closed position of the jaw member. In this case, a lifting over the entire range of movement can be prevented by the undercut. Otherwise, it is also sufficient if a lifting of the components from each other is only prevented by the undercut when no clip is present in the passage region, as the clip otherwise can prevent a lifting of the components from one another.

According to a further advantageous embodiment of the first aspect of the present invention, the cam support member carries at least one cam, which at least over a part of the axial displacement of the cam support member to the link member abuts a link member, which is formed on the link member. The cam has on an axial cross-section side, which faces the link path, substantially a Z-shape, an S-shape or a combination thereof. In this case the cam forms a belly and groove, wherein the groove can enter into a part of the link member to form together with the belly an undercut. In this way a lifting of the cam support member from the link member can be prevented. Of course a lifting of the link member from the cam support member can also be prevented in the same manner.

According to a further advantageous embodiment of the first aspect of the present invention, the cam support member carries at least one cam, which at least over a part of the axial displacement of the cam support member to the link member abuts a link member, which is formed on the link member. The link path has on the axial cross-section side, which faces the cam, substantially a Z-shape, an S-shape or a combination thereof. With this setup a lifting of the cam support member and the link member from each other over the region of mutual movement can be prevented, by that a mutual undercut of the two components is formed. For the undercut it is for both the cam and the link member advantageous when the belly and the associated groove of the components together form a Z-shape, an S shape or a combination thereof. It is further advantageous when the two cross-sectional shapes of cam and link path substantially correspond to each other. In this case, the tendency to the mutual self-locking of the two components can be reduced or even eliminated.

According to an advantageous embodiment of the first aspect of the present invention, the cam and the link path exhibit on their respective mutually facing sides of their cross section substantially an S-shape. The cam and the link path form in this manner a belly and a groove respectively and the belly of a component protrudes respectively into the groove of the other component. The S-shape is particular advantageous as these dimensions which the components described herein have are easier to manufacture and during the installation it is not as vulnerable as the Z-form. The same goes also for other possible forms, such as a step shape for example, thus as a belly formed with right angles and a corresponding groove.

According to a further advantageous embodiment of the first aspect of the present invention a straight portion is formed between the belly and groove of the cam and/or the link path. On this straight portion of the cross section the contact of the two components takes substantially place. In the direction of extension of the cam and/or the link path this portion doesn't need be straight. In this direction it is more likely that a curvature of the cam and/or the link path is present. This straight portion of the cam and/or the link path is preferably inclined relative to the opening/closing direction of the jaw member, more preferably more than 7°, in particular less than 20°. When the two components abut one another, a force is generated which is transverse to the longitudinal axis of the jaw member. This is also necessary in order to control an opening or closing operation of the jaw member. If an inclination is formed at the abutting portion of the two components, the introduced shear creates a resultant force which urges the two components towards each other. This prevents a lifting of the two components from each other. From an angle of 7° with the dimensions of the components a production of the components is simplified, because they need to be formed less delicate. Above an angle of 20°, the friction increases excessively, without necessarily implying a particular advantage.

According to a further advantageous embodiment of the first aspect of the present invention, the curvature of the belly of the link path is larger than the curvature of the groove of the link path and/or the curvature of the belly of the cam is larger than the curvature of the groove. To simplify, one can say that the groove is always a little larger than the received belly therein. With the term curvature here the average curvature of the respective component is meant. The curvature can naturally change along the groove or the belly, it can even have steps (i.e., in the groove or the belly is a kink formed), but in the given case is at least in the region in which the groove and belly touch each other the curvature of the belly larger than that of the groove. Larger curvature means the radius is smaller, which leads to that along a cross section through the cam and the link portion only at most one contact region between the cam and the link member is formed. If the curvature of the groove would be larger than that of the therein received belly, two contact regions would be formed, which would lead to an unnecessary increased friction between the two components against each other. Furthermore this would also lead to that the belly spreads open the respective groove, which can lead to a deformation of the other belly or even a crack formation along the groove.

Further advantageously, the curvature of the belly of the link path is larger than the curvature of the groove of the cam and/or the curvature of the belly of the cam is larger than the curvature of the groove of the link path.

According to another advantageous embodiment of the first aspect of the present invention, the direction of force application from the cam against into the link path opposite to the opening/closing direction of the jaw member is inclined, preferably in a range of up to 20°. This is equivalent to saying that the contact point between the cam and link path is formed in a region which is inclined with respect to the opening/closing direction of the jaw member, preferably up to 20°. As described above, only one contact region is formed at the described curvature of belly and groove of the components, which, when a certain difference in the two relevant curvatures is present, can also be referred to as contact point. In a theoretical consideration only one contact point is formed at an infinitesimal difference in the curvature of the two components concerned, in practice however the elasticity of the components leads to the fact that a defined contact point is formed only when the difference in the curvature reaches a certain difference.

According to an advantageous embodiment of the first aspect of the present invention, the surface of the cam in the region of the contact point with the link path is facing the central axis of the cam support member. With such a configuration, the transmitted forces in the region of the groove and the belly exhibit a direction which proceed substantially towards the central axis of the cam support member. In this way, only relative small torsional moments are generated. Great torsion moments, which could damage the jaw member, can lead to a distortion at the filigree components.

According to an advantageous embodiment of the first aspect of the present invention, at least one link member extending substantially over the entire width of the cam support member, so that the respective cam of the cam support member is substantially covered through the corresponding link member. For the opening and closing movement of the jaw member a lateral contact of cam and link path is crucial. For a better mutual guidance of link member and cam support member it can be advantageous if the link member covers the cam. In this way, the possible resulting torsional forces can also be transmitted even better, so that it doesn't come to a distortion of the cam support member.

According to an advantageous embodiment of the first aspect of the present invention at least one link member comprises at least two link paths, which with a corresponding number of cams on the cam support at least form an respective undercut over a part of the axial displacement of the two components to each other from a fully open position to a fully closed position of the jaw member, wherein said cam support member and link member can be exclusively assembled by the undercut, by turning them into each other. The inwardly turning assembly here refers to a rotation of one component relative to the other component in the plane in which the opening and closing of the jaw member takes place. At least one of the components can be so elastic that during the rotation at first at one position it comes into contact with another component during the rotation and then is bent elastically, before it comes into the undercut at a second point. After that it can be elastically deformed back.

Alternatively thereto the assembling can be carried out with parallel longitudinal axes of the components. This requires a position of the components concerned to each other, in which no undercuts are formed. In this position, the components are brought together and subsequently slide in the axial direction to form undercuts. Especially advantageous is the mounting position outside the working range of the components, so that during the operation always an undercut between the affected components is present nevertheless.

By the above embodiment of at least one undercut over the entire range of mutual movement of the link member and the cam support member, these two components cannot simply be set on top of each other with substantially parallel longitudinal axes. On top of each other here refers to the layered structure, wherein the direction of a touchdown is perpendicular or normal to the surface of the individual layers.

Since the cam support member also comprises at least one cam and a link member has formed link paths on both sides in many embodiments, these two components cannot be placed easily laterally to each other.

The complex setup leads among other things to a special assembly of the jaw member. A link component and said cam supporting component are arranged in two parallel planes, wherein the longitudinal axes of these components engage a certain angle to each other within the parallel planes. Now, the two components are joined to each other until they come into contact. In this state, the two components form a sort of inclined cross or St. Andrew's cross. In this state, the two components are now so twisted to each other that their longitudinal axes of the components have substantially the same direction thereafter. This process is referred to herein as inwardly turning, and the assembly as inwardly turning assembly. With such an inwardly turning assembly it is in fact impossible that the jaw member, when it is installed in a shaft of a tubular shafted instrument, can be dismantled into its individual components. In addition, no separate component is required to maintain the integrity of the components. When the cam support member is fixable, for example with a snap fit like a dovetail connection, to a feeding element of the tube shafted instrument and the link members are designed for example with elastic mounted projections, which can snap into corresponding recesses in the tubular shaft of a tubular shafted instrument, then a completely tool-free and mounting material free assembly of the jaw member and attachment thereof to a tubular shaft of a tubular shafted instrument is possible.

According to a further advantageous embodiment of the first aspect of the present invention reside the link member and the cam support member after an inwardly turning assembly in a mounting position which is outside of the relative axial displacement of the link member and the cam support member to each other from a fully open position to a fully closed position of the jaw member. The position of the components to each other will be changed during the mounting on a tubular shaft, so that the mounting position is transferred into an initial position of the jaw member for a closing operation (or opening operation at a spreading instrument or the like). In the snap connections described above, this for example can be achieved when the connection between the link members and tubular shaft wall is first prepared, and only a little later, that means after a certain distance, the connection between the cam support member and the feeding element is established. Then during the mounting occurs a displacement between the link member and the cam support member. Typically, one jaw member is mounted on a tubular shaft by inserting the jaw member assembly consisting of the cam support member and the link members from distal into the front end of the tubular shaft.

According to a second aspect of the present invention, a jaw member for a surgical tubular shafted instrument shows a first branch having a first active region and a second branch having a second active region. The first branch and the second branch have a respective link member and the branches are held in the axial direction. A cam support member is provided which is slideable relative to the link members in the axial direction, wherein the link members are formed substantially planar and are substantially arranged layerlike one above the other and the cam support member has a substantially hollow cross section, in which the link members are arranged.

In contrast to the first aspect of the present invention, the second aspect shows so-called inner link members. These are so called because they are surrounded by the cam support member when in the mounted state. The general principle of the jaw member control corresponds to the first embodiment of the present invention. Also in this embodiment, a support member can be provided or the link members are held by a member of a tubular shaft.

According to an advantageous embodiment of the second aspect of the present invention the link member and the cam support member can be brought from a mounting position by an axial movement relative to each other into a fully open position.

The fully open position corresponds to the initial position or zero position, beyond which in the mounted state there is no relative displacement possible between the two components.

According to the invention therefore a jaw member with the aforementioned features or individually claimable feature combinations is suggested that belongs to the pivot type without axis/without bolts, thus having no objective pivot axis.

According to a third aspect of the present invention, a method for the assembling of a branch and a cam support member for an above-described jaw member is disclosed which comprises the following steps. First, a branch and a cam support member are provided in a state in which a link member of the branch is facing the associated side of the cam support member. The term associated in this case means that the shape and position of the link path or link paths of the branch and the shape and position of the cam or cams of the cam support member are coordinated to each other so that they can cause an opening operation and closing operation of the two components to each other. Thereby the branch and the cam support member are arranged in two parallel planes which are spaced to each other, and the longitudinal axes of the two components take a certain angle between them. This angle in turn depends on the shape and position of the cam(s) and link path(s). The cam(s) and the link path(s) project from the respective base surface of the cam support member or the link member of the branch. The particular angle is therefore chosen so that there is no superposition of a cam with a link path forming region. Subsequently, the branch and the cam support member are introduced to each other until they come in contact. Because there is no superposition between a cam and a link path forming region, a contact of the two base areas of link member and cam support member is carried out. Now, the branch and the cam support member are rotated relative to each other in the through their contact surface determined plane in such a way that the angle between their longitudinal axes decreases. Strictly speaking, there is no point of intersection between the longitudinal axes of the two components. The aforesaid angle is the angle formed by the longitudinal axes of the two components when they are projected in parallel into the contact plane of link member and cam support member. This plane is determined by the base area of the two components. The rotation of the two components against each other is continued until at least one respective cam of the cam support member on both sides of the crossing point of the two longitudinal axes comes in contact with a link path. In this manner a further rotation is prevented. During the rotation, a displacement of one of the components or of the two components along their longitudinal axes can also take place, so that the movement of the components to each other is not purely rotational. However, it is crucial that a rotational component is contained in the mutual movement of the two components. Furthermore during the movement, preferably at least one undercut between a cam and a link member can be formed.

Preferably, the at least one link member and the cam support member are formed substantially planar and are superimposed substantially layerlike.

With this method, a particularly simple, fast, tool-free and cost-effective assembly of the jaw member is made possible. The thus formed assembly of the jaw member can be processed further easily.

According to a fourth aspect of the present invention, a method for assembling a surgical tubular shafted instrument is disclosed. The tubular shafted instrument comprises an above-described jaw member, a shaft member and an actuating rod. The assembly starts with a provision of a branch and a cam support member in a state in which a link member of a branch facing the associated side of the cam support member. The one branch and the cam support member are arranged in two parallel planes which are spaced from each other, and the longitudinal axes of the two components determine a certain angle between them. This is done in accordance with the third aspect of the present invention, wherein the explanation given there regarding the angles applies, in this aspect. Subsequently said one branch and the cam support member are introduced to each other until they are in contact. After that said one branch and the cam support member are rotated relative to each other in the through their contact surface determined plane in such a way that the angle between their longitudinal axes is reduced until at least one respective cam of the cam support member on both sides of the crossing point of the two longitudinal axes comes in contact with a link member of the one branch. The method further discloses an attachment of another branch on the opposite side of the cam support member. However, this can also happen before the aforementioned method steps, so that the other branch can also be the first branch mounted on the cam support member. This other branch can either be mounted in the same manner on the cam support member, as described above for said one branch, the branch can also be mounted entirely different. When the other branch for example, should be held immobile, said branch can be simply placed on the cam support member without that a rotational movement between the other branch and the cam support component is required. In this case, the cam support member for example can exhibit two or more fungiform projections, which can be inserted respectively into a round hole in the link member of the other branch, of which in the axial direction an elongated hole extends with a width, which corresponds substantially to the diameter of the shaft of the fungiform projections. Thus an axial relative movement between the cam support member and the other branch is possible, without that any lateral movement of the components to each other results. Also other known connecting mechanisms may be used. In principle it is also possible that no other branch is mounted, since this one for example is formed at the distal end of the shaft member. After mounting of the jaw member, this is inserted with its proximal end in a distal end of the shaft member. Thereby said one branch and/or the other branch as well as the cam support member intervene at different times with one of the shaft member or the actuating rod, so that therefore between the cam support member and the one branch and/or the other branch an axial displacement takes place to a position which corresponds to the fully open position of the jaw member. If the two branches are similarly mounted onto the cam support member, it is advantageous when they also come into engagement at about the same time with the shaft member or the actuating rod. It is preferred here when the branches come into engagement with the shaft member and the cam support member with the operating rod. Further preferably at first the cam support member comes into engagement with the actuation rod, whereby a further axial displacement of the cam support component to proximal is prevented. The branch or branch(s) may then be shifted even further proximal until they engage with the shaft member. A branch comprising therefore preferably a proximally extending resilient extension which pushes the proximal end of the branch to the inner wall of the shaft member. At the inner wall of side which is facing the shaft member the extension has at least one projection which can enter a recess or deepening in the shaft member to establish a connection between the branch and the shaft member. According to an further advantageous development, on the side facing away from the inner wall of the shaft member of the extension an area is formed which cooperates with a corresponding surface on the cam support member so that the area at the relative displacement of branch and cam support member by or during the mounting at that time to which the least one projection on the extension of the branch has entered into the recess in the shaft member and the branch therefore is axially fixed to the shaft member, an undercut is formed, so that the extension at the branch cannot move nearer to the axis of the shaft member, that the at least one projection on the extension of the branch can completely come out of the recess in the shaft member. Since the cam support member, when it was once attached to the operating rod, no longer can be moved to distal that this undercut can be given up with the extension of the branch, thus dismantling the jaw member is reliably prevented by the shaft member.

Preferably, the at least one link member and the cam support member are designed substantially planar and are superimposed substantially layerlike.

With the described method a tubular shafted instrument can be provided, which can be assembled especially easy, which after an assembly cannot be disassembled and in which a lifting of a link member from the cam support member is securely prevented.

Alternatively to the above-described way of assembling of the two link members and of the cam support member, there are other variations. In a first alternative variant, the two link member s are elastically bendable in the plane in which they substantially extend. In this case the link members can be bent in their extension plane, so that there exist no superposition between the link paths and the cams of the cam support member, and then they can be guided to the cam support member. Only when the link member comes into contact with the cam support member, the link members are relax back to their original shape, wherein the undercut is then formed between the link paths and the cams. In a second alternative variation, the link members are provided with interruptions which are only slightly larger than the associated cams. These interruptions are arranged so that there is a relative arrangement of the cam support member and the link member in which all the cams of the cam support member faces a corresponding recess. In this relative arrangement, the link member and the cam support member can be brought together, wherein the cams enter through the recesses into the link paths. At a relative axial displacement of the two components to each other the undercuts then are formed between link paths and the cams. It is advantageous if the relative arrangement for the assembly is located outside of a region in which the two components in an ordinary operation move to each other. In a third alternative variation, the link members are vertically resiliently flexible to their plane of extension. Furthermore the link members exhibit the recesses mentioned above in the link paths, only that these are not arranged at the same intervals as those of the cams. In this variation, a link member for the assembling with the cam support member is bent out of the extension plane, a first cam is threaded into a first link path through a first recess. Afterwards the cam support member and link member are mutual displaced axially until a second cam of a second recess is on the opposite side. Now this second cam is threaded through the second recess into the second link path, wherein this portion of the link path is bent back into its original position. If appropriate further other cams are threaded in the same manner into the link path. The advantage of this variation is that there is no relative position of the cam support member and link member to each other, in which the two components can be disassembled without an elastic deformation onto the link member must be applied. This embodiment is thus secured against falling apart accidentally.

BRIEF DESCRIPTION OF THE DRAWING FIGURES

Further advantages and features of the invention are apparent to the person skilled in the art from the accompanying drawings and the detailed description of the embodiments.

FIG. 1A shows an isometric view of a first embodiment of a first branch of the jaw member according to the first aspect of the present invention, shown in a regular position of the first branch;

FIG. 1B shows an isometric view of the first branch of the jaw member of FIG. 1A shown tilted by 90° to the outside tilted position;

FIG. 2A shows an isometric view of a first embodiment of a second branch of the jaw member according to the first aspect of the present invention, shown in a regular position of the second branch;

FIG. 2B shows an isometric view of the second branch of the jaw member of FIG. 2A shown tilted by 90° to the outside tilted position;

DETAILED DESCRIPTION

The embodiments of the various aspects of the present invention are described below with reference to the figures.

Referring to FIGS. 1A to 7B, a first embodiment of the first aspect of the present invention is described in detail in the following.

Figure 3A:
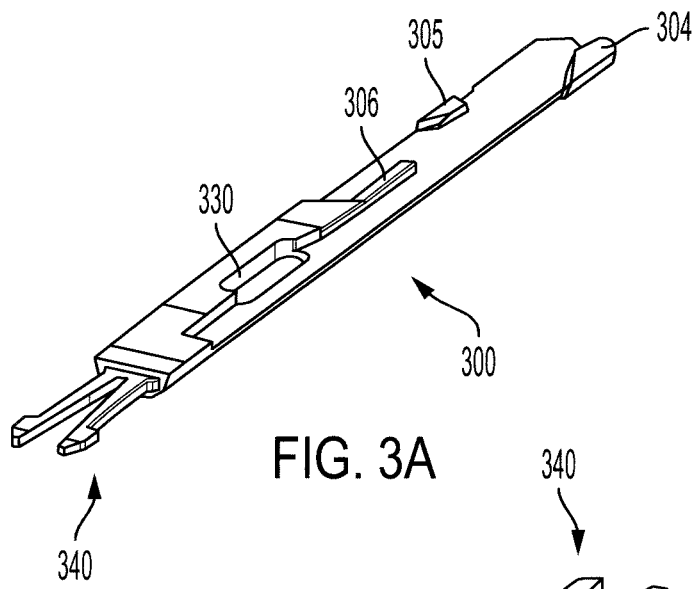
FIG. 3A shows a proximal isometric view of a first embodiment of a cam support member of the jaw member according to the first aspect of the present invention.
Figure 3B:
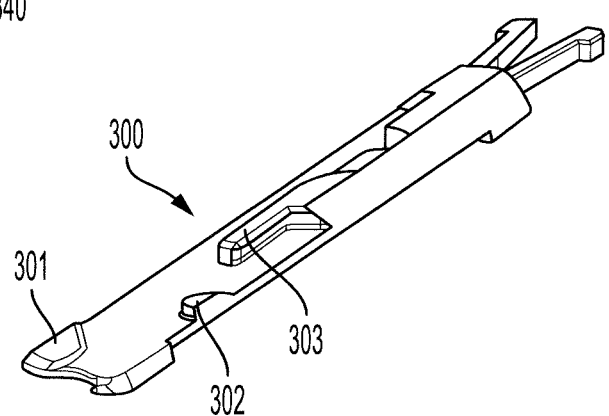
FIG. 3B shows a distal isometric view of the cam support member of the jaw member of FIG. 3A.
Figure 4:
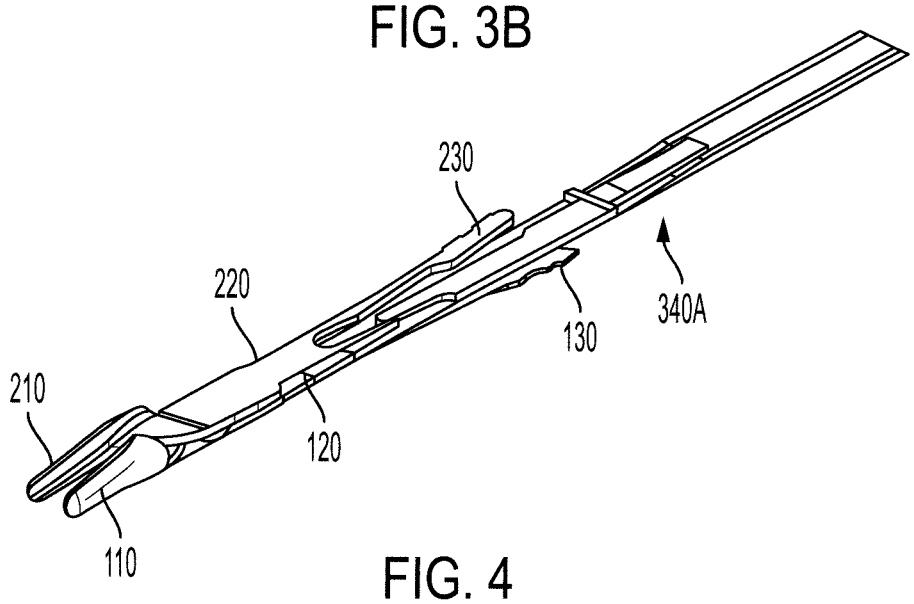
FIG. 4 shows an isometric view of the jaw member including a portion of an operating rod of a tubular shafted instrument according to FIGS. 1A-3B.

In FIG. 4, a jaw member 1 for a surgical tubular shafted instrument is shown. The tubular shafted instrument is a surgical clip applying forceps for double shank clips, which are also called ring clips due to their manufacturing process. In the present case the clip applying forceps is designed for the serially applying of a plurality of clips. Such a clip applying forceps is called multi fire clip applicator or clip applicator of the multi fire kind. At this clip applicator a magazine of double shank clips is provided of which a next clip is inserted from proximal to the jaw member 1 after the application of a clip, so that the next application can be immediately carried out immediately subsequently.

The jaw member comprises a first branch 100 with a first active region 110 and a second branch 200 with a second active region of 210. The first branch 100 and second branch 200 each have a link member 120, 220 and the branches 100, 200 are held in the axial direction. A cam support member 300 is positioned slideable relative to the two link members 120, 220 in axial direction and the two link members 120, 220 and the cam support member 300 are formed substantially planar and are arranged substantially layerlike one above the other. The cam support member 300 and the link members 120, 220 have a plurality of regions in which they form an undercut. In this way, a lifting of the link members 120, 220 from the cam support member 300 is reliably prevented. An region of an undercut between each link member 120, 220 and the cam support member 300 remains over the entire range of movement of the link members 120, 220 to the cam support member 300 from a fully open position, as shown in FIG. 4, up to a fully closed position of the jaw member 1 preserved. This means that over the entire range of movement of each respective link member 120, 220 to the cam support member 300 always at least one undercut between the two affected components is formed, wherein in several places undercuts can also be formed temporary and a single undercut exists optionally only over a certain portion of the relative movement.

The cam support member 300 in this embodiment carries six cams 301 to 306. Each of these cams 301 to 306 is located over at least a portion of the axial displacement of the cam support member 300 to the respective link member 120, 220, on a link path 121, 122, 123, 224, 225 and 226, which is formed on the link member 120, 220. The cams 301 to 306 have on each side of their axial cross-section which is facing the link path 121, 122, 123, 224, 225, 226 a substantially S-shape, wherein this shape is not shown in FIGS. 1 and 2 for reasons of clarity. Suitable for that the axial cross sections of the link paths 121, 122, 123, 224, 225, 226 have on the side which is facing the respective cam 301 to 306 also have substantially an S-shape. This form is not shown in FIGS. 3A and 3B for reasons of clarity. Therefore, in FIG. 5, the shapes of the cams 301, 304 and the associated link paths 121, 224 for all cams and link paths of this embodiment are shown exemplified.

Figure 5:
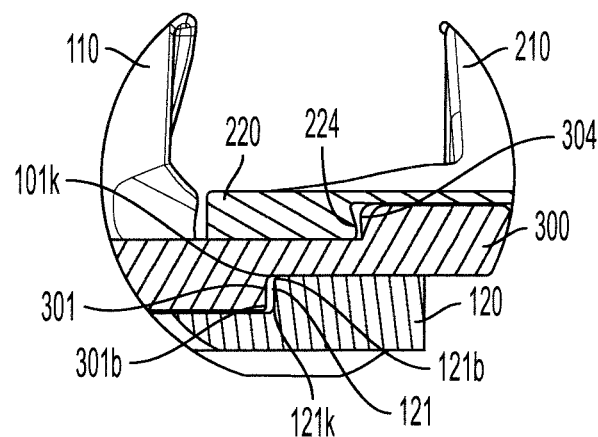
FIG. 5 shows a sectional view of the jaw member according to FIG. 4.

As can be seen from FIG. 5, the cams 301 to 306 and the link paths 121, 122, 123, 224, 225, 226 forming in this way one belly and one groove respectively. Shown in detail is this in FIG. 5 for the link member 121, which forms a belly 121b and a groove 121k, and for the associated cam 301, which forms a belly 301b and a groove 301k. The belly 301b projects into the groove 121k and the belly 121b projects into the groove 301k, wherein an undercut is formed in this way. Especially clearly shown is this in FIG. 8 of for a second embodiment, which is described later.

As can be seen from FIGS. 4 and 5, the link member 220 extends substantially over the entire width of the cam support member 300, so that the cam 304 of the cam support member 300 is substantially covered by the link member 220.

As already described above, in this embodiment, each link member 120, 220 comprises three link paths 121, 122, 123 or 224, 225, 226 which are with three cams 301 to 303 and 304 to 306 respectively on the cam support member 300 over at least a part of the axial displacement of the two components to each other from a fully open position to a fully closed position of the jaw member 1 in an undercut. Thereby is the cam support member 300 and each of the two link members 120, 220 can be exclusively assembled by an inwardly turning of the link member 120, 220 into the cam support member 300. How this works out in detail is described in FIG. 6. Below the assembly for the branch 100 is shown. In the present embodiment, the assembly with the branch 200 is carried out in the same way.

Figure 6A:
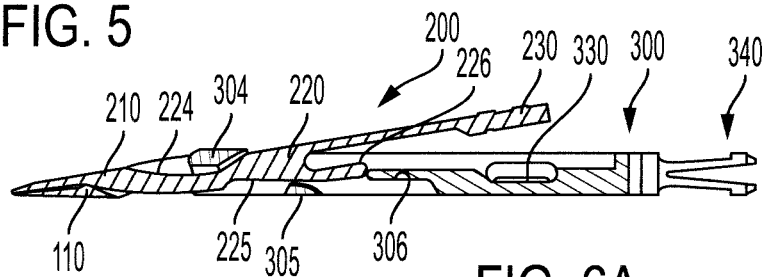
FIGS. 6A-6D shows plan views of the jaw member according to FIG. 4 during a mounting of a first jaw member.
Figure 6B:
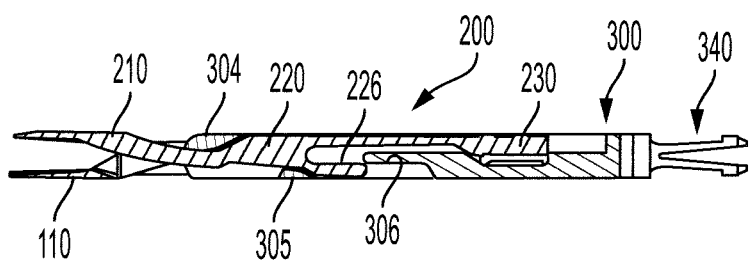

First, the branch 100 and the cam support member 300 are provided in a state in which the link member 120 of the branch 100 faces the associated side of the cam support member 300. The branch 100 and the cam support member 300 are arranged in two parallel planes which are spaced apart from each other, and the longitudinal axes of the two members 100, 300 take an angle of approximately 10° into between them. Subsequently, the branch 100 and the cam support member 300 are brought together until they are in contact, as shown in FIG. 6A. Usually, the branch 100 is moved toward the cam support member 300, it can also be that the cam support member 300 is moved towards the branch 100. Subsequently, the branch 100 is rotated relative to the cam support member 300 in the plane which is defined by its contact area in such a way that the angle between their longitudinal axes decreases. The branch 100 is rotated until the link path 224 comes into contact with the cam 304 and the link path 225 comes into contact with the cam 305, as is shown in FIG. 6B. As it can also be seen from FIG. 6A, the two cams 304, 305 and the two link paths 224, 225 lie on opposite sides of the crossing point of the longitudinal axes of the two components 200, 300.

Figure 6C:
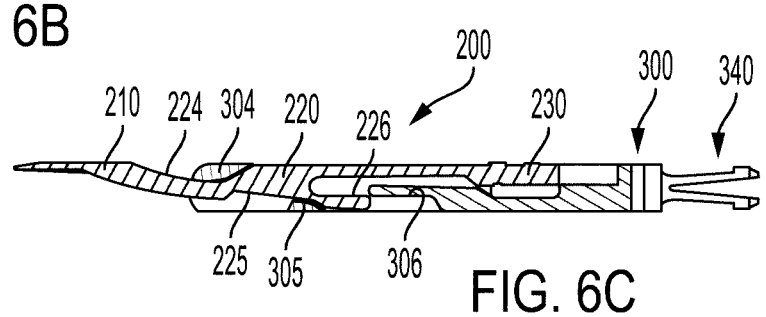
Figure 6D:
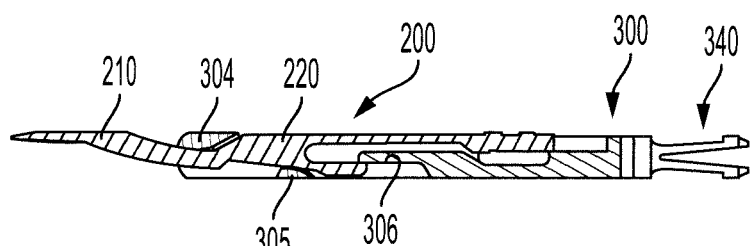

In the position shown in FIG. 6B the link member 220 and the cam support member 300 are in a mounting position after the inwardly turning assembly. This mounting position is outside of the relative axial displacement of the link member 220 and the cam support member 300 to each other from a fully open position to a fully closed position of the jaw member 1 and is characterized in that an extension 130, 230, which is provided at each branch 100, 200 and which is laterally resilient against to the respective link member 120, 220 is, that means it can move elastically in an arc away from and towards the longitudinal axis of the component, with its proximal end can dip into a recess 330, which is formed in the cam support member 300. When the proximal end of the extension 230 dips into this recess 330, then the lateral projections 231, 232 of the extension 230 are shifted so far towards the longitudinal axis of the branch 200 that the assembled jaw member 1 can be inserted into a distal end of the tubular shaft of a tubular shafted instrument. While inserting the distal end of the extension 230 pushes outwardly against the wall of the tubular shaft. In the tubular shaft wall two recesses are provided which are adapted to receive the two projections 231, 232. When the projections 231, 232 slide in these recesses in the tubular shaft wall, the branch 200 is held relative to the tubular shaft wall axially, so that at a further insertion of the jaw member 1 into the tubular shaft, only moves the cam support member 300. Here it is assumed that the other branch 100 has a comparable setup as the branch 200 shows and the projections 131, 132 engage at the same time into the corresponding recesses in the tubular shaft wall. Then the pushing rod is inserted from proximal into the tubular shaft until the clasp 340 of the cam support member 300 engages into a corresponding receptacle in a receptacle formed in the pushing rod. The pushing rod is arranged in the tubular shaft in order to cause an actuation of the jaw member 1. The moment in which the projections 231, 231 dip into the recesses in the tubular shaft wall is shown in FIG. 6C. In FIG. 6D can be seen that a relative displacement between branch 200 and cam support member 300 has taken place, so that the distal end of the extension 230 cannot dip into the recess 330 anymore. At the same time, since the cam support member 300 is axially held by the pushing rod, these can no longer be moved further distal than shown in FIG. 6D. This setup enables a tool-free installation, which requires only very small forces and thereby creating a setup which cannot be dismantled without destruction.

The jaw member 1 can thus, as described above, be brought by an axial movement of the link member 220 relative to the cam support member 300 from a mounting position in a fully open position. The fully open position is also the zero position of the clip applicator.

Figure 7A:
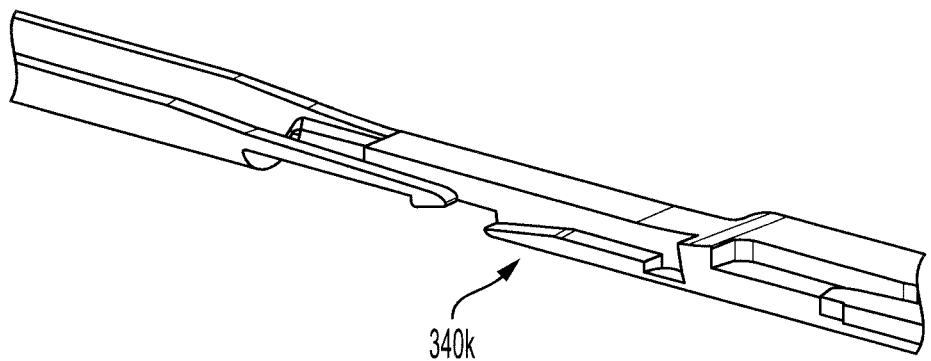
FIGS. 7A and 7B show isometric views of a proximal end of a second embodiment of the cam support member according to the first aspect of the present invention and the distal end of an actuating rod of a tubular shafted instrument.
Figure 7B:
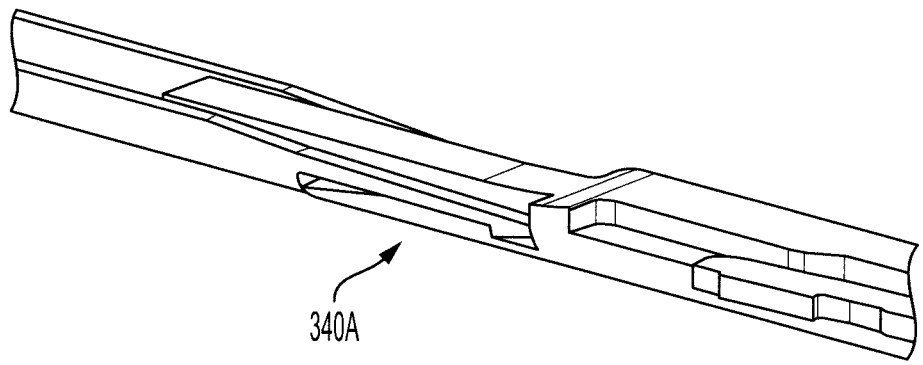

A second embodiment of the first aspect of the present invention is described in detail with reference to FIGS. 7A, 7B and 8.

The jaw member 1 according to the second embodiment has substantially the same setup as the first embodiment, only the differences in comparison to the first embodiment are explained here.

The clasp 340A, with which the cam support member 300 is attachable to the pushing rod of the tubular shafted instrument is configured in such a way that the two arms are not elastically deformable towards each other anymore, but rather that these are parallel upwardly deformable, in order to slide over the corresponding counterparts on the actuating rod and to engage with them. With this setup the mounting of the jaw member onto a tubular shaft requires lower mounting forces. At the same time with this setup greater actuating forces can be transmitted compared to the clasp 340 of the first embodiment.

Moreover, in the second embodiment, the undercuts between link paths and cams are formed stronger.

Both the link paths and the cams of this embodiment have a cross-section, which equates to an S-shape rather than this is the case in the first embodiment.

Figure 8:
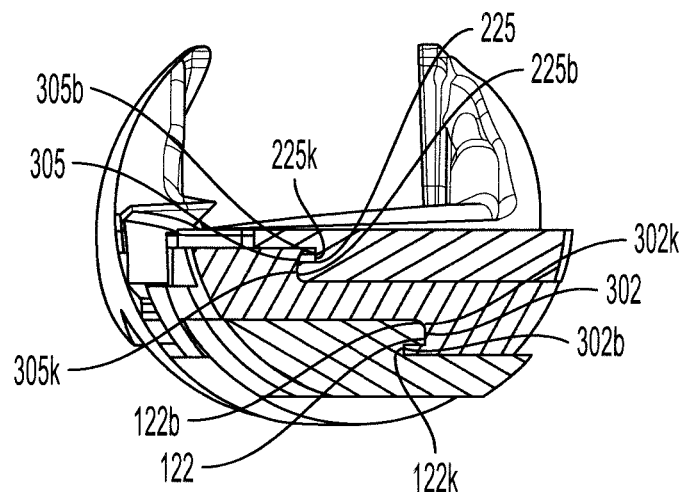
FIG. 8 shows a sectional view of a second embodiment of the jaw member according to the first aspect of the present invention.

In addition in FIG. 8 it is shown, that the curvature of the belly 122*b*, 225*b* of the link path 122, 225 is smaller than the curvature of the groove 122*k*, 225*k* of the link path 122, 225 and the curvature of the belly 302*b*, 305*b* of the cam 302, 305 is larger than the curvature of the groove 302*k*, 305*k* of the cam 302, 305. Even more the curvature of the belly 122*b*, 225*b* of the link path 122, 225 is larger than the curvature of the groove 302*k*, 305*k* of the cam 302, 305, and the curvature of the belly 302*b*, 305*b* of the cam 302, 305 is larger than the curvature of the groove 122*k*, 225*k* of the link path 122, 225 is. This means that the belly is always more curved than the groove, in which it is received. In this manner between belly and groove in the cross section only a single contact point is formed and there is no spreading effect of the belly in the groove. At more than one contact point in the cross section the sliding of the link member and the cam support member along each other would be inhibited and the friction would increase strongly. Furthermore a too big belly in a too small groove could lead to cracks forming in the groove which would destroy the corresponding component.

Another feature of this embodiment is that the contact point between the cam 302, 305 and link path 122, 225 is formed in a region which is inclined relative to the opening/closing direction of the jaw member. In this way the force between the link member 120, 220 and cam support member 300 is securely transmitted in the region of link paths and it comes to an unnecessary increase of the friction between these components. Unnecessary friction can occur when the sandwich structure of link members 120, 220 and cam support member 300 is pressed together. This in turn can happen easily when the force transmittance occurs too close to the edges of the in cross-sectional view curved link paths and cams.

Figure 9:
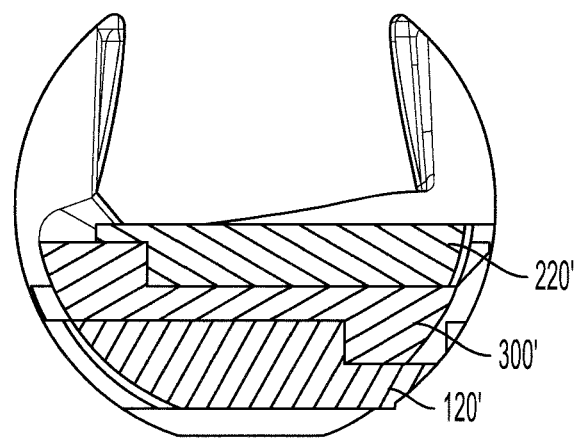
FIG. 9 shows a sectional view of a third embodiment of the jaw member according to the first aspect of the present invention.

A third embodiment of the first aspect of the present invention is described in detail with reference to FIG. 9.

In this embodiment no undercuts are formed between the link members 120', 220' and the cam support member 300'. Rather, the cams 301 to 306 and the link paths 121, 122, 123, 224, 225, 226 are formed as vertical walls which protrude in a right angle from the sandwich planes of the mouth part 1. The sandwich planes are parallel to the plane in which the opening and closing operation of the jaw member takes place. With such a setup it must be prevented by other means that the link members 120', 220', lift from the cam support member 300'. The remaining setup of this embodiment corresponds to that of the first embodiment.

Figure 10:
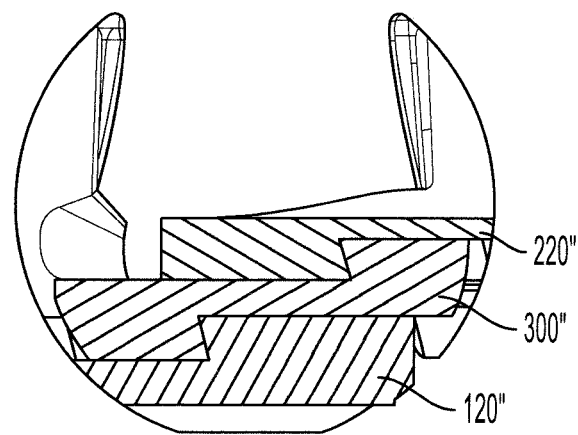
FIG. 10 shows a sectional view of a fourth embodiment of the jaw member according to the first aspect of the present invention.

A fourth embodiment of the first aspect of the present invention is described in detail with reference to FIG. 10.

In this embodiment, the cams 301 to 306 and the link paths 121, 122, 123, 224, 225, 226 are formed in such a way, that they have in cross-section a Z-form. Even with such a structure, a lifting of the link members 120", 220" from the cam support member 300" is securely prevented. The rest of the structure corresponds to that of the first embodiment.

Figure 11:
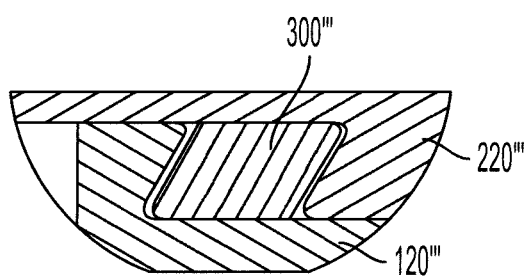
FIG. 11 shows a sectional view of a fifth embodiment of the jaw member according to the first aspect of the present invention.

A fifth embodiment of the first aspect of the present invention is described in detail with reference to FIG. 11.

In this embodiment, the cams 301 to 306 of the cam support member 300" are displaced towards the central axis, so that the cam support member is also received laterally between the link members 120''', 220'''. The link paths 121, 122, 123, 224, 225, 226 and the cams 301 to 306 are also formed so that they have a Z-shape in cross section, which have rounded edges. One can also call this shape an S-shape having a straight central portion. Even with such a structure a lifting of the link members 120''', 220''' from the cam support member 300''' is securely prevented. The rest of the structure corresponds to that of the first embodiment.

Figure 12:
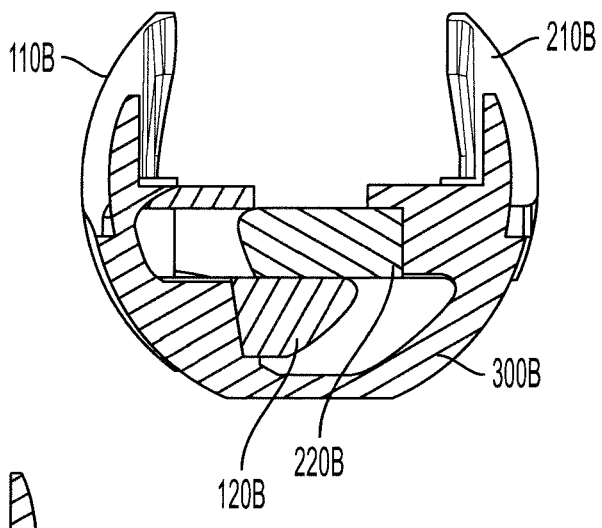
FIG. 12 shows a sectional view of a sixth embodiment of the jaw member according to a second aspect of the present invention.
Figure 13:
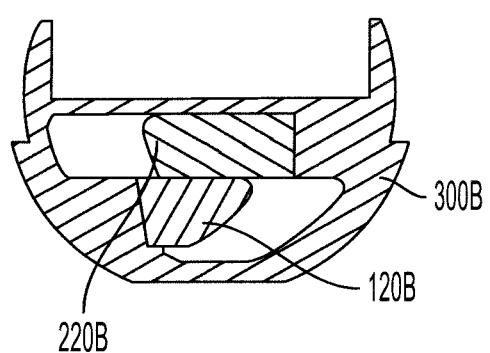
FIG. 13 shows a sectional view through the link members and the cam support member according to FIG. 12.
Figure 14:
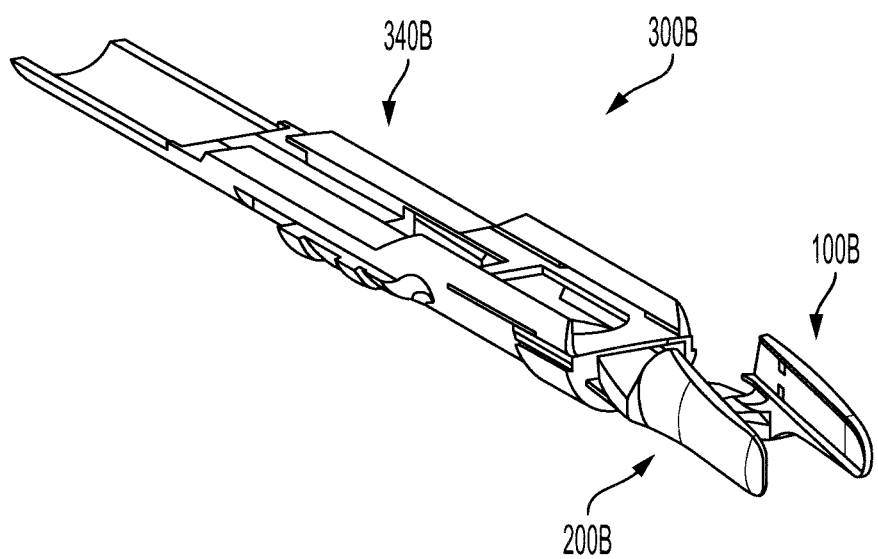
FIG. 14 shows an isometric view of the sixth embodiment of a jaw member according to the second aspect of the present invention.

A sixth embodiment of the first aspect of the present invention is described in detail with reference to FIGS. 12 to 14.

Unlike the preceding embodiments, in the sixth embodiment, the branches 100B, 200B or their link members 120B, 220B are received in the cam support member 300B. One speaks in this case of an external cam support member 300B. In this embodiment, the branches 100B, 200B are mounted on the cam support member 300B by being inserted from distal into the cam support member 300B. A lifting of the link members 120B, 220B from the cam support member 300B cannot occur in this embodiment. The cam support member 300B can therefore be formed more massive, but this is at the costs of the link members 120B, 220B.

About the embodiments and modifications shown here in detail it for a person skilled in the art many other advantageous combinations are apparent which are also object of the present application.

The invention claimed is:

1. A jaw member for a tubular shafted surgical instrument, the jaw member comprising:
    a first branch having a first active region; and
    a second branch having a second active region,
    the first branch comprising a first link member and the second branch comprising a second link member, the first and second branches held in an axial direction,
    the jaw member further comprising a cam support member which is slideable relative to the first link member and the second link member in the axial direction, and
    the first link member, second link member and the cam support member formed substantially planar and arranged substantially sandwichlike in a three-layer structure, with the first link member beneath the cam support member, and the cam support member beneath the second link member, and with the first link member separated from the second link member by the cam support member.

2. The jaw member according to claim 1, wherein the cam support member and the first link member have at least one region in which they form an undercut so that a lifting of the first link member from the cam support member is prevented, wherein at least one region of the undercut is present over the entire range of movement of the first link member to the cam support member from a fully open position to a fully closed position of the jaw member.

3. The jaw member according to claim 2,
    wherein
    the cam support member carries at least one cam which abuts at a link path, which is formed on the first link member, over at least a part of an axial displacement of the cam support member to the first link member, wherein the at least one cam on a link path-facing side of the at least one cam's axial cross-section substantially has a Z-shape, an S-shape or a combination thereof.

4. The jaw member according to claim 3, wherein
the at least one cam and the link path have at the respective facing sides of their cross-section a substantially a S-shape, and the at least one cam and the link path in this way each form one belly and one groove, the belly of one of the at least one cam and the link path respectively protrudes in the groove of the other of the at least one cam and the link path.

5. The jaw member according to claim 4, wherein
a straight portion is formed between the belly and the groove of the at least one cam and/or of the link path, wherein the straight portion is inclined relative to an opening/closing direction of the jaw member more than 7° and less than 20°.

6. The jaw member according to claim 4, wherein
a curvature of the belly of the link path is smaller than a curvature of the groove of the link path and/or a curvature of the belly of the at least one cam is larger than a curvature of the groove of the cam.

7. The jaw member according to claim 4, wherein
a curvature of the belly of the link path is larger than a curvature of the groove of the cam and/or a curvature of the belly of the at least one cam is larger than a curvature of the groove of the link path.

8. The jaw member according to claim 3, wherein
the first link member substantially extends over an entire width of the cam support member, so that a respective cam of the cam support member is substantially covered through the second link member.

9. The jaw member according to claim 2, wherein
the cam support member carries at least one cam which abuts at a link path, which is formed on the first link member, over at least a part of an axial displacement of the cam support member to the first link member, wherein
the link path on a cam-facing side of an axial cross-section of the link path substantially has a Z-shape, an S-shape or a combination thereof.

10. The jaw member according to claim 2, wherein
a direction of force application from the at least one cam into the link path is inclined relative to an opening/closing direction of the jaw member, in a range of up to 20°.

11. The jaw member according to claim 10, wherein
a surface of the at least one cam in a region of a contact point with the link path is facing a central axis of the cam support member.

12. A jaw member for a tubular shafted surgical instrument, the jaw member comprising:
a first branch having a first active region; and
a second branch having a second active region,
the first branch comprising a first link member and the second branch comprising a second link member, the first and second branches held in an axial direction, the jaw member further comprising a cam support member which is slideable relative to the first link member and the second link member in the axial direction, and
the first link member, second link member and the cam support member formed substantially planar and arranged substantially sandwichlike in a three-layer structure, with the first link member beneath the cam support member, and the cam support member beneath the second link member,
wherein the cam support member and the first link member have at least one region in which they form an undercut so that a lifting of the first link member from the cam support member is prevented, wherein at least one region of the undercut is present over the entire range of movement of the first link member to the cam support member from a fully open position to a fully closed position of the jaw member,
wherein the undercut comprises a plurality of undercuts, wherein the first link member comprises at least two link paths, and the cam support member comprises a corresponding number of cams which with said at least two link paths at least over a part of an axial displacement of the first link member and the cam support member to each other from the fully open position to the fully closed position of the jaw member form said plurality of undercuts, wherein the cam support member and the first link member can be exclusively assembled by screwing the cam support member and the first link member into each other.

13. The jaw member according to claim 12, wherein
the first link member and the cam support member are, after an inward-turning assembly, in a mounting position which is outside of a relative axial displacement of the first link member and the cam support member to each other from the fully open position to the fully closed position of the jaw member.

14. A jaw member according to claim 1, wherein
the jaw member is of the pivot type without an axis.

15. A method for assembling a branch and a cam carrier member for the jaw member according to claim 1, comprising the steps of:
providing a branch of the first or second branch and the cam support member in a state in which the link member of the branch is facing the associated side of the cam support member, wherein said branch and the cam support member are arranged in two parallel planes which are spaced from each other, and the longitudinal axes of the two components engage a certain angle between them;
advancing of the branch and the cam support member to each other until they are in contact; and
turning the branch and the cam support member relative to each other in the through their contact surface specified plane in the manner that the angle between their longitudinal axes is reduced, until at least one respective cam of the cam support member on either sides of the crossing point of the two longitudinal axes comes into contact with a link path.

16. A method for assembling a surgical tubular shafted instrument with the jaw member according to claim 1, a shaft member, and an actuating rod, the method comprising the steps of:
providing a branch of the first or second branch and the cam support member in a state in which the link member of the branch is facing the associated side of the cam support member, wherein said branch and the cam support member are arranged in two parallel planes which are spaced from each other, and the longitudinal axes of the two components engage a certain angle between them;

advancing the branch and the cam support member to each other until they are in contact;

turning the branch and the cam support member relative to each other in the through their contact surface specified plane in the manner that the angle between their longitudinal axes is reduced, until at least one respective cam of the cam support member on either sides of the crossing point of the two longitudinal axes comes into contact with a link path of the branch;

attaching the other branch of the first or second branch on the opposite side of the cam support member, wherein this step can also be done at the beginning of the method; and inserting the proximal end of the thus produced jaw member in a distal end of the shaft member, wherein the first branch and/or the second branch and the cam support member come at different times into engagement with one of the shaft member or the actuating rod so that therefore an axial displacement between the cam support member and the first branch and/or the second branch in a position takes place which corresponds to the fully open position of the jaw member.

* * * * *